(12) United States Patent  
Motoyama et al.

(10) Patent No.: US 9,932,308 B2  
(45) Date of Patent: **\*Apr. 3, 2018**

(54) METHOD FOR PRODUCING INDOLINE COMPOUND

(71) Applicant: UBE INDUSTRIES, LTD., Ube-shi, Yamaguchi (JP)

(72) Inventors: Takahiro Motoyama, Ube (JP); Katsunori Takata, Ube (JP); Yasuaki Fukuhara, Ube (JP); Masato Uemura, Ube (JP); Tatsunori Sado, Ube (JP); Atsuyuki Kasai, Ube (JP)

(73) Assignee: UBE INDUSTRIES, LTD., Ube-shi (JP)

( \* ) Notice: Subject to any disclaimer, the term of this patent is extended or adjusted under 35 U.S.C. 154(b) by 0 days.

This patent is subject to a terminal disclaimer.

(21) Appl. No.: 15/472,860

(22) Filed: Mar. 29, 2017

(65) Prior Publication Data

US 2017/0197917 A1    Jul. 13, 2017

Related U.S. Application Data

(62) Division of application No. 15/115,452, filed as application No. PCT/JP2015/052705 on Jan. 30, 2015, now Pat. No. 9,643,921.

(30) Foreign Application Priority Data

Feb. 6, 2014 (JP) ................................. 2014-021679  
Jun. 18, 2014 (JP) ................................. 2014-125489  
Oct. 9, 2014 (JP) ................................. 2014-207653

(51) Int. Cl.  
C07D 209/08   (2006.01)

(52) U.S. Cl.  
CPC .................................. C07D 209/08 (2013.01)

(58) Field of Classification Search  
CPC ............................ C07D 209/12; A61K 31/404  
See application file for complete search history.

(56) References Cited

U.S. PATENT DOCUMENTS 7,834,193 B2    11/2010  Yamaguchi et al.  
8,471,039 B2     6/2013  Joshi et al.  
(Continued)

FOREIGN PATENT DOCUMENTS

CN      1699331 A    11/2005  
CN    101048376 A    10/2007  
(Continued)

OTHER PUBLICATIONS

May 30, 2017 Search Report issued in European Patent Application No. 15745991.8.  
(Continued)

*Primary Examiner* — Golam M Shameem  
(74) *Attorney, Agent, or Firm* — Oliff PLC

(57) ABSTRACT

Provided is a salt including a compound represented by a formula (4) and a compound represented by a formula (5). A method for producing the salt includes reacting a compound represented by a formula (2) with a compound represented by a formula (3) in the presence of a quaternary onium salt and a base to form the compound represented by the formula (4); and mixing the compound represented by the formula (4) with the compound represented by the formula (5). A method for producing a compound represented by a formula (6) includes removing, from the salt including the compounds of formulae (4) and (5), a protecting group $P^1$. In the following formulae, $P^1$ and $P^2$ are both protecting groups.

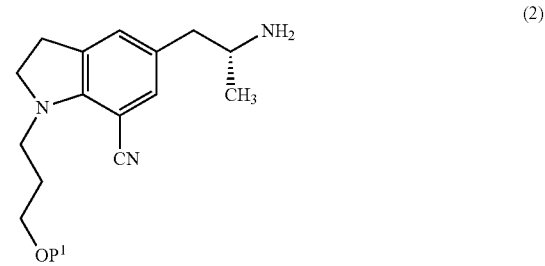

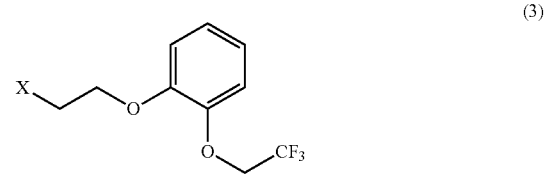

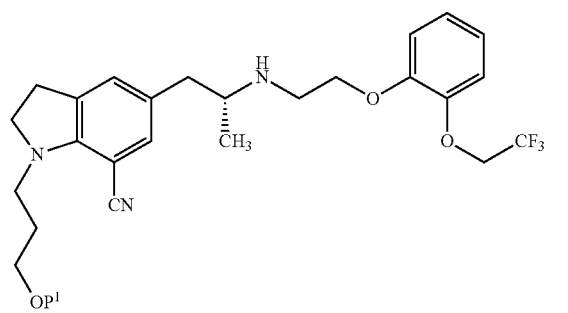

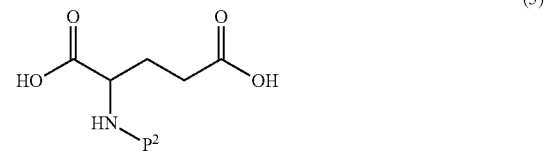

(Continued)

-continued (6)

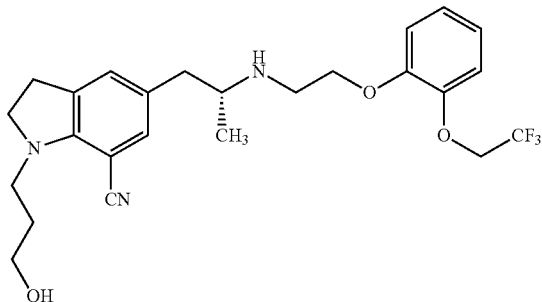

5 Claims, No Drawings

(56) References Cited

U.S. PATENT DOCUMENTS

| | | | |
|---|---|---|---|
| 9,643,921 B2 * | 5/2017 | Motoyama | C07D 209/12 |
| 2005/0261376 A1 | 11/2005 | Lerestif et al. | |
| 2006/0142374 A1 | 6/2006 | Tsuru et al. | |
| 2007/0197627 A1 | 8/2007 | Yamaguchi et al. | |
| 2010/0274018 A1 | 10/2010 | Bleda et al. | |

FOREIGN PATENT DOCUMENTS

| | | |
|---|---|---|
| CN | 101412690 A | 4/2009 |
| CN | 101772475 A | 7/2010 |
| CN | 102382029 A | 3/2012 |
| JP | 2005-330263 A | 12/2005 |
| JP | 4532274 B2 | 8/2010 |
| JP | 2010-535177 A | 11/2010 |
| JP | 5049013 B2 | 10/2012 |
| WO | 2006/046499 A1 | 5/2006 |
| WO | 2012/147019 A1 | 11/2012 |

OTHER PUBLICATIONS

Apr. 21, 2015 International Preliminary Report on Patentability issued in International Patent Application No. PCT/JP2015/052705.

U.S. Appl. No. 15/115,452, filed Jul. 29, 2016 in the name of Motoyama et al.

Apr. 21, 2015 International Search Report issued in International Patent Application No. PCT/JP2015/052705.

Aug. 9, 2016 International Preliminary Report on Patentability issued in International Patent Application No. PCT/JP2015/052705.

\* cited by examiner

METHOD FOR PRODUCING INDOLINE COMPOUND

CROSS REFERENCE TO RELATED APPLICATIONS

This is a Division of application Ser. No. 15/115,452, filed Jul. 29, 2016, which in turn is a 371 of PCT/JP2015/052705, filed Jan. 30, 2015, which claims priority to JP 2014-207653, filed Oct. 9, 2014, JP 2014-125489, filed Jun. 18, 2014, and JP 2014-021679, filed Feb. 6, 2014. The disclosure of the prior applications is hereby incorporated by reference herein in its entirety.

TECHNICAL FIELD

The present invention relates to a method for producing an indoline compound.

BACKGROUND ART

As a method for producing (−)-1-(3-hydroxypropyl)-5-[(2R)-2-({2-[2-(2,2,2-trifluoroethoxy)phenoxy]ethyl}amino)propyl]-2,3-dihydro-1H-indole-7-carboxamide (generic name: silodosin, which may hereinafter be referred to as "compound (1)"), there is known, for example, a method in which: a compound represented by formula (A) and a compound represented by formula (B) are reacted to obtain a compound represented by formula (C) (3-{7-cyano-5-[(2R)-2-({2-[2-(2,2,2-trifluoroethoxy)phenoxy]ethyl}amino)propyl]-2,3-dihydro-1H-indol-1-yl}propyl benzoate); then the benzyl group is removed to produce a compound represented by the formula (D) (7-cyano-1-(3-hydroxypropyl)-5-[(2R)-2-({2-[2-(2,2,2-trifluoroethoxy)phenoxy]ethyl}amino)propyl]-2,3-dihydro-1H-indole); and further the cyano group is converted into an amide group through hydrolysis to produce the compound (1) (see Patent Literature 1, for example).

[Chemical Formula 1]

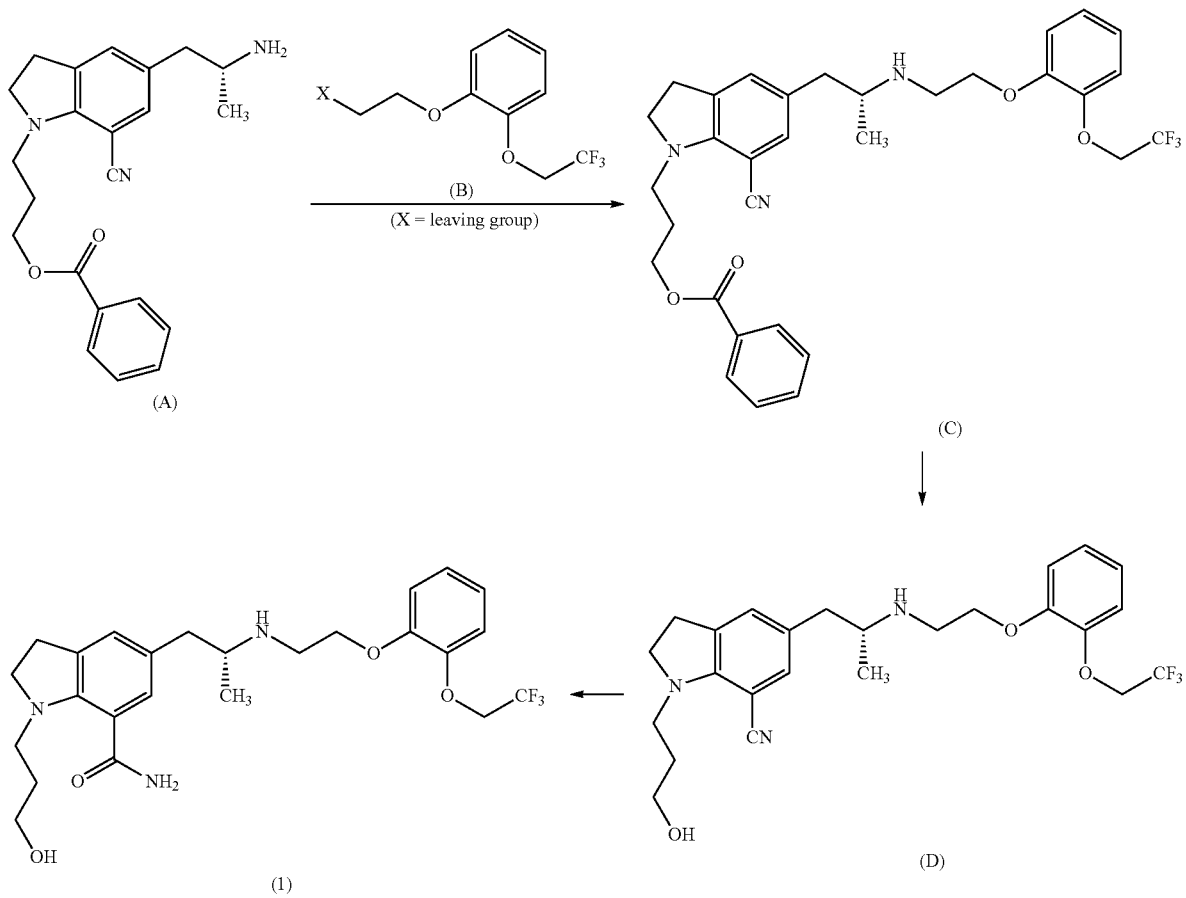

In the meantime, three crystal forms, α-crystal, β-crystal, and γ-crystal, are known for the compound (1) (see Patent Literature 3, for example). In particular, Patent Literature 3 discloses that the α-crystal is white and that the α-crystal is beneficial as a crystal for oral solid medicine in terms of hygroscopicity and stability.

CITATION LIST

Patent Literature

Patent Literature 1: JP 5049013 B
Patent Literature 2: WO 2012/147019
Patent Literature 3: JP 4532274 B

SUMMARY OF INVENTION

Technical Problem

In the method for producing the compound (1), a compound (E-1), a compound (E-2), and a compound (E-3) may be formed as impurities.

[Chemical Formula 2]

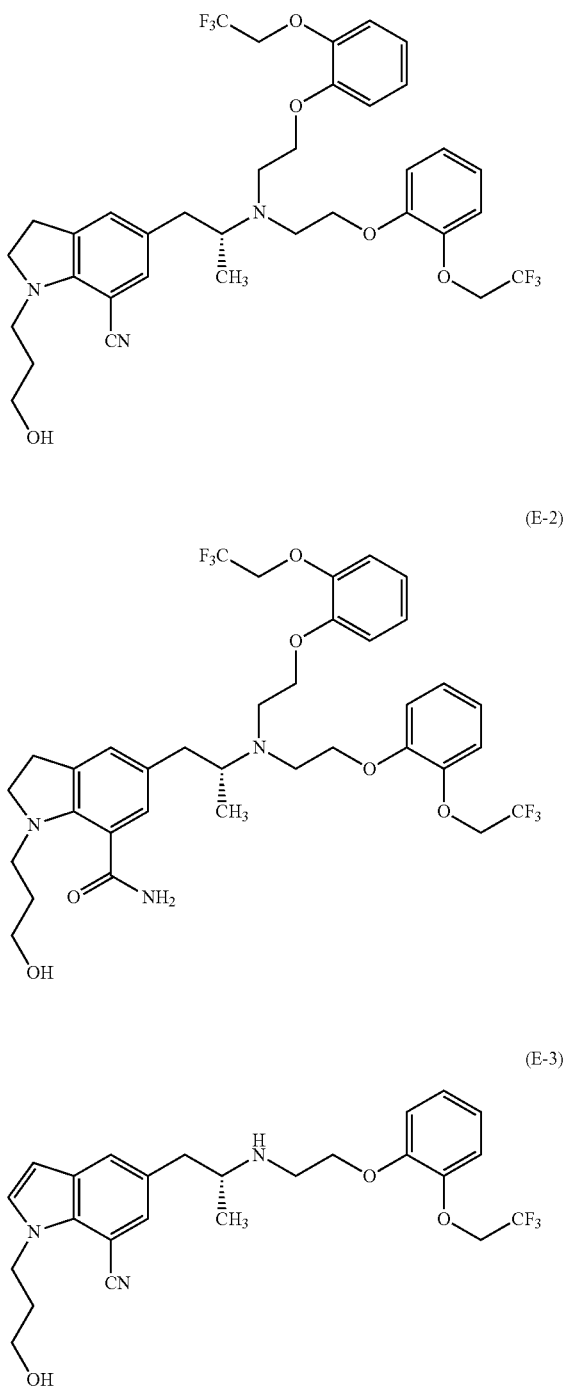

The compound (E-1) is formed when 2 moles of the compound (B) reacts with 1 mole of the compound (A) in the reaction between the compound (A) and the compound (B), followed by the leaving reaction of the benzoyl group. The compound (D) and the compound (E-1) are similar to each other in chemical properties and thus are difficult to separate by a common purification means such as a column. In addition, the compound (E-1) is converted into the compound (E-2) when the subsequent step is performed using a mixture of the compound (D) and the compound (E-1). The compound (E-2) is also similar to the compound (1) in chemical properties, and they are thus difficult to separate from each other.

In relation to the above circumstances, Patent Literatures 1 and 2 disclose methods in which the compound (D) is crystallized in the form of its oxalic acid salt or L-tartaric acid salt to remove the compound (E-1) and thus obtain the compound (D) of higher purity.

However, the methods described in Patent Literatures 1 and 2 cannot necessarily give an adequate yield of the compound (1) and may fail to achieve sufficient removal of the compound (E-1). For example, in the method using oxalic acid, the content of the compound (E-1) is 0.9% (see Example 1 of Patent Literature 1), while in the method using L-tartaric acid, the yield of the compound (D) is low although the content of the compound (E-1) is 0.10 to 0.16% (see Patent Literature 2).

In addition, the crystal of the oxalic acid salt of the compound (D) is disadvantageous in terms of ease of handling since the crystal is highly hygroscopic and readily absorbs atmospheric moisture as crystallization water. In the meanwhile, L-tartaric acid has been reported to inhibit intestinal absorption of phosphorus and calcium.

Furthermore, Patent Literature 2, in which crystallization of salts of the compound (D) with various acids is attempted, demonstrates that a solid salt is not formed when using: polycarboxylic acids such as malonic acid, succinic acid, citric acid, and fumaric acid; esters such as tartaric acid diester; amino acids such as L-lysine; and inorganic acids such as hydrochloric acid and sulfuric acid.

The compound (E-3) is a compound resulting from oxidation of the indoline structure of the compound (1). The compound (E-3) can be formed under various oxidizing conditions in the course of production or purification of the compound (1) or its crystal.

The present inventors have conducted a detailed study on the stability of an α-crystal of the compound (1) and, as a result, have found problems in that oxidation of the indoline structure is induced by heat or light, causing the formation of a large amount of the compound (E-3) and also in that transformation into another crystal form is likely to occur under a physical stimulus such as crushing.

In view of the above circumstances, the present invention aims to provide methods for obtaining the compound (1) and its crystal of higher purity and provide a crystal of the compound (1) of higher purity.

Solution to Problem

The present invention provides the following [1] to [15].

[1] A method for producing a compound represented by a formula (6),

[Chemical Formula 5]

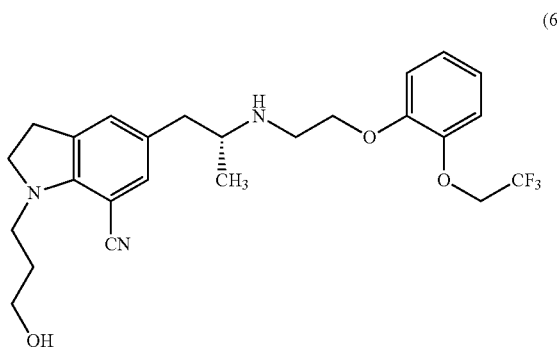
(6)

the method comprising:
a step of mixing a compound represented by a formula (4)

[Chemical Formula 3]

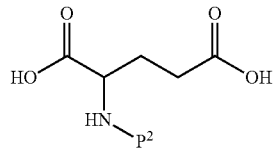
(4)

wherein $P^1$ is a protecting group, and a compound represented by a formula (5)

[Chemical Formula 4]

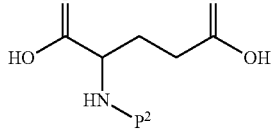
(5)

wherein $P^2$ is a protecting group, to form a salt consisting of the compound represented by the formula (4) and the compound represented by the formula (5); and
a step of removing the protecting group $P^1$ of the salt.

[2] The method according to [1], wherein the compound represented by the formula (5) is N-acylglutamic acid.

[3] A salt comprising:
a compound represented by a formula (4)

[Chemical Formula 6]

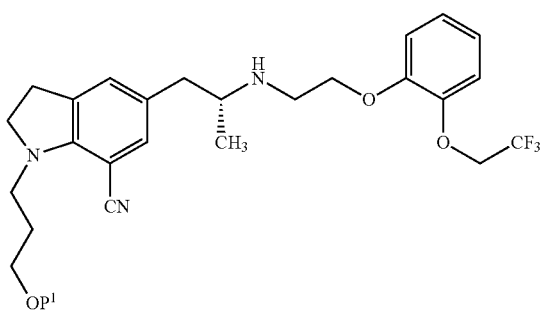
(4)

wherein $P^1$ is a protecting group; and
a compound represented by a formula (5)

[Chemical Formula 7]

(5)

wherein $P^2$ is a protecting group.

[4] The salt according to [3], wherein the compound represented by the formula (5) is N-acylglutamic acid.

[5] A method for producing a compound represented by a formula (4)

[Chemical Formula 10]

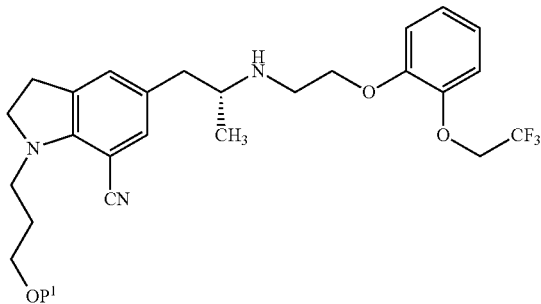
(4)

wherein $P^1$ is a protecting group,
the method comprising a step of reacting a compound represented by a formula (2)

[Chemical Formula 8]

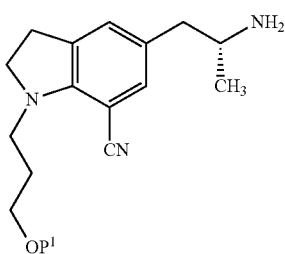

(2)

wherein P¹ is a protecting group, and a compound represented by a formula (3)

[Chemical Formula 9]

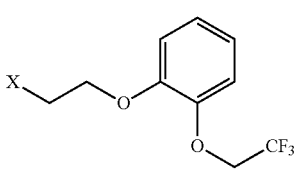

(3)

wherein X is a leaving group, in the presence of a quaternary onium salt and a base.

[6] The method according to [5], wherein the quaternary onium salt is a quaternary ammonium chloride or a quaternary ammonium bromide.

[7] A method for producing a γ-crystal of a compound represented by a formula (1),

[Chemical Formula 11]

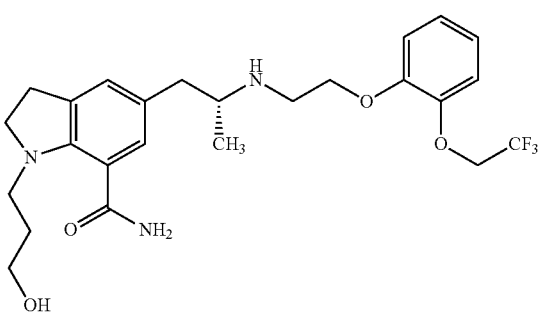

(1)

the method comprising crystallizing the compound represented by the formula (1) in an alcohol solvent represented by a formula (7)

[Chemical Formula 12]

ROH  (7)

wherein R is an alkyl group having 1 to 4 carbon atoms, or in a mixed solvent of the alcohol solvent and an ether solvent represented by a formula (8)

[Chemical Formula 13]

ROR¹  (8)

wherein R is an alkyl group having 1 to 4 carbon atoms and R¹ is a branched or cyclic alkyl group having 3 to 6 carbon atoms.

[8] The method according to [7], wherein the alcohol solvent is at least one solvent selected from the group consisting of methanol, ethanol, isopropyl alcohol, and t-butyl alcohol.

[9] The method according to [7] or [8], wherein the ether solvent is at least one solvent selected from the group consisting of diisopropyl ether, t-butyl methyl ether, and cyclopentyl methyl ether.

[10] The method according to any one of [7] to [9], further comprising adding a γ-crystal of the compound represented by the formula (1) in an amount of 1 to 50 mg relative to 1 g of the compound represented by the formula (1) to the alcohol solvent or the mixed solvent dissolving the compound represented by the formula (1).

[11] A γ-crystal of a compound represented by a formula (1), wherein the crystal is obtained by the method according to any one of [7] to [10].

[Chemical Formula 14]

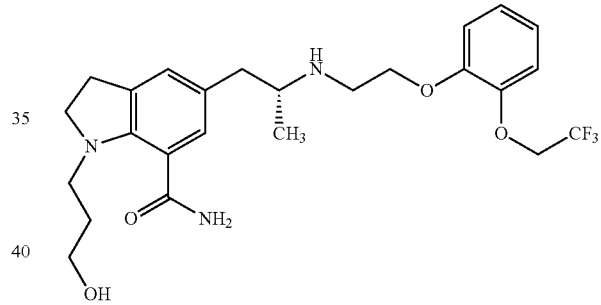

(1)

A γ-crystal of a compound represented by a formula (1), the crystal optionally comprising as an impurity a compound represented by a formula (E-3)

[Chemical Formula 15],

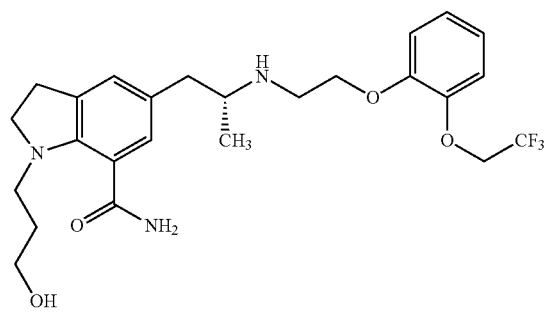

(1)

-continued (E-3)

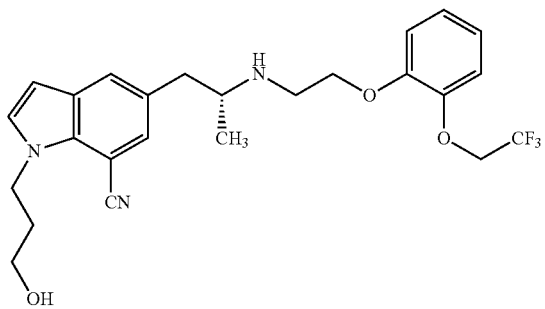

wherein when a content of the compound represented by the formula (E-3) with respect to a total amount of the crystal is expressed as X % and a content of the compound represented by the formula (E-3) as measured after heating of the crystal at 70° C. for 192 hours is expressed as Y %, [Y−X] (a difference between Y and X) is less than 0.040%.
[13] The crystal according to [12], wherein the crystal optionally comprises a solvent as an impurity, and
a content of the solvent is 890 ppm or less with respect to the total amount of the crystal.
[14] The crystal according to [12] or [13], wherein the content of the compound represented by the formula (E-3) is 0.001 to 0.200% with respect to the total amount of the crystal.
[15] The crystal according to any one of [12] to [14], wherein the content of the compound represented by the formula (E-3) is a value calculated on the basis of peak areas in a chromatogram as obtained by detection using high-performance liquid chromatography at a wavelength of 225 nm.
[16] An oral medicine for treatment of dysuria, comprising the crystal according to any one of [11] to [15] as an active ingredient.

Advantageous Effects of Invention

With the present invention, it is possible to provide an efficient method for producing the compound (4) useful as an intermediate for the synthesis of the compound (1) serving as a dysuria treatment agent.

With the present invention, it is possible to provide an efficient method for producing the compound (5) useful as an intermediate for the synthesis of the compound (1) serving as a dysuria treatment agent.

With the present invention, it is possible to provide a γ-crystal with good stability of the compound (1) and a method for producing the same. The γ-crystal with good stability of the compound (1) according to the present invention is a crystal that contains a small amount of remaining solvent and that is stable to heat, light, and crushing.

DESCRIPTION OF EMBODIMENTS

The following gives a detailed description by presenting embodiments of the present invention. In the specification, compounds represented by the formula (1) and the other formulae may be referred to as "compound (1)" and the like for the sake of convenience.

A "crystal" refers to a structure in which specific molecules are spatially arranged in a lattice in such a manner as to achieve translational symmetry, and does not refer to only a structure consisting of a single compound. The γ-crystal of the compound (1) in the present specification may contain a solvent or the like in addition to the compound (1), as described in Patent Literature 3. In particular, "α-crystal", "β-crystal", and "γ-crystal" are each identified by a method described in Patent Literature 3 and, specifically, the identification is performed through measurement of powder X-ray diffraction.

An embodiment of the present invention is a method for producing the compound (1). This method comprises step A, step B1, step B2, and step C. Each of the steps will hereinafter be described in detail.

[Chemical Formula 16]

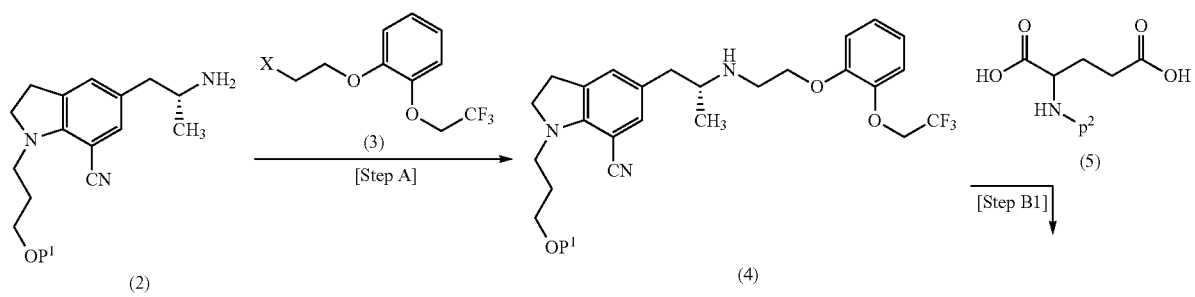

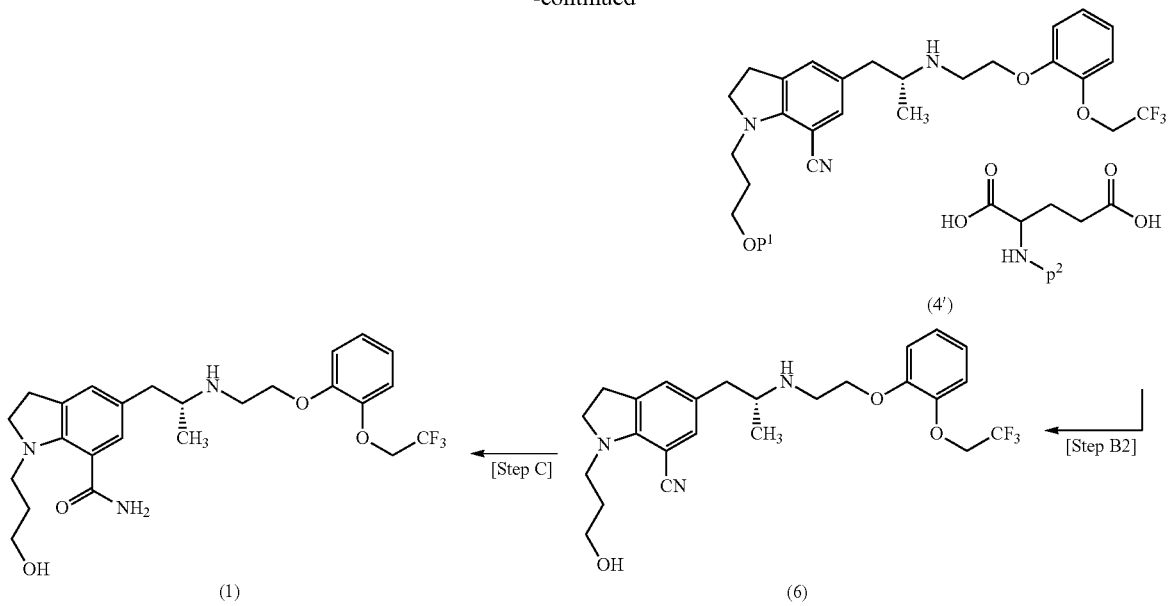

(4')

[Step B2]

(6)

[Step C]

(1)

[Step A]

This step is a step of reacting a compound (2) and a compound (3) in the presence of a quaternary onium salt and a base to form a compound (4)

[Chemical Formula 17]

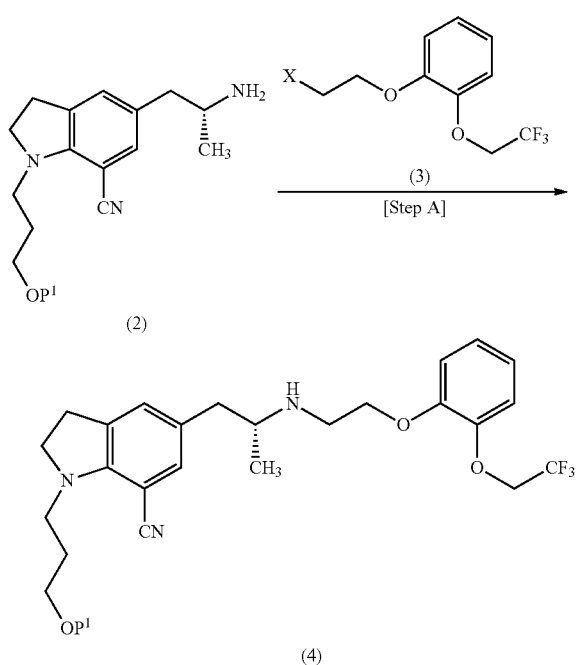

(2)

(3)

[Step A]

(4)

wherein $P^1$ is a protecting group and X is a leaving group.

Compound (2)

For the formula (2), $P^1$ is not particularly limited as long as it is a protecting group for a hydroxy group, and examples thereof include: alkyl groups such as a methyl group and a t-butyl group; aralkyl groups such as a benzyl group (Bn) and a p-methoxybenzyl group (PMB); acyl groups such as an acetyl group (Ac), a pivaloyl group (Piv), and a benzoyl group (Bz); a trimethylsilyl group (TMS); a t-butyldimethylsilyl group (TBDMS); a triisopropylsilyl group (TIPS); and a t-butyldiphenylsilyl group (TBDPS), and $P^1$ is preferably an aralkyl group or an acyl group and more preferably a benzyl group or a benzoyl group.

It should be recalled that the compound (2) can be used also in the form of a salt. In this case, the compound (2) may be used after being converted into a free form beforehand or may be converted into a free form in a liquid reaction mixture.

Compound (3)

In the formula (3), X is a leaving group, and examples thereof include: halogen atoms such as fluorine, chlorine, bromine, and iodine; and hydrocarbylsulfonyloxy groups such as a methanesulfonyloxy group, an ethanesulfonyloxy group, a benzenesulfonyloxy group, and a p-toluenesulfonyloxy group.

The amount of the compound (3) used is preferably 1.05 to 1.30 moles and more preferably 1.1 to 1.25 moles relative to 1 mole of the compound (2). When the amount of the compound (3) used is within this range, it is possible to prevent only one of the materials (the compound (2) or the compound (3)) from remaining excessively in the reaction liquid after completion of the reaction.

Quaternary Onium Salt

Examples of the quaternary onium salt include: quaternary ammonium chlorides such as ammonium chloride, tetramethylammonium chloride, tetraethylammonium chloride, tetrapropylammonium chloride, tetrabutylammonium chloride, tetrapentylammonium chloride, tetrahexylammonium chloride, tetraheptylammonium chloride, and tetraoctylammonium chloride; quaternary ammonium bromides such as ammonium bromide, tetramethylammonium bromide, tetraethylammonium bromide, tetrapropylammonium bromide, tetrabutylammonium bromide, tetrapentylammonium bromide, tetrahexylammonium bromide, tetraheptylammonium bromide, and tetraoctylammonium bromide; quaternary phosphonium chlorides such as phosphonium chloride, tetramethylphosphonium chloride, tetraethylphosphonium chloride, tetrapropylphosphonium chloride, tetrabutylphosphonium chloride, tetrapentylphosphonium chloride, tetrahexylphosphonium chloride, tetraheptylphosphonium chloride, and tetraoctylphosphonium chloride; and quaternary phosphonium bromides such as phosphonium bromide, tetramethylphosphonium bromide, tetraethylphosphonium bromide, tetrapropylphosphonium bromide, tetrabutylphosphonium bromide, tetrapentylphosphonium bromide, tetrahexylphosphonium bromide, tetraheptylphosphonium bromide, and tetraoctylphosphonium bromide, and the quaternary onium salt is preferably a quaternary ammonium chloride or a quaternary ammonium bromide. These quaternary onium salts may be used alone or two or more thereof may be used as a mixture.

The amount of the quaternary onium salt used is preferably 0.05 to 0.30 moles and more preferably 0.05 to 0.10 moles relative to 1 mole of the compound (2). When the amount of the quaternary onium salt used is within this range, the quaternary onium salt can be dissolved or dispersed uniformly in the reaction liquid, providing a sufficient reaction speed.

Base

Examples of the base used in step A include: alkali metal hydroxides such as sodium hydroxide and potassium hydroxide; alkali metal carbonates such as sodium carbonate and potassium carbonate; alkali metal hydrogen carbonates such as sodium hydrogen carbonate and potassium hydrogen carbonate; alkali metal alkoxides such as sodium methoxide, sodium ethoxide, potassium methoxide, and potassium ethoxide; and organic bases such as triethylamine and diisopropylmethylamine, among which an alkali metal carbonate is preferably used. These bases may be used alone or two or more thereof may be used as a mixture.

The amount of the base used is preferably 1.00 to 1.50 moles and more preferably 1.05 to 1.20 moles relative to 1 mole of the compound (2). When the amount of the base used falls within this range, it is possible to promote the reaction and also to sufficiently trap an acid resulting from the reaction.

Organic Solvent

Step A may be performed in the absence of any solvent or may be performed in the presence of an organic solvent. The organic solvent is not particularly limited as long as it does not inhibit the reaction. Examples of the organic solvent used in step A include: alcohols such as methanol, ethanol, n-propyl alcohol, isopropyl alcohol, and t-butyl alcohol; carboxylic acid esters such as ethyl acetate, isopropyl acetate, and butyl acetate; nitriles such as acetonitrile and propionitrile; amides such as N,N-dimethylformamide and N,N-dimethylacetamide; sulfoxides such as dimethyl sulfoxide and diethyl sulfoxide; and aromatic hydrocarbons such as toluene and xylene, and the organic solvent is preferably nitriles or amides. These organic solvents may be used alone or two or more thereof may be used as a mixture.

The amount of the organic solvent used is preferably 4 to 15 mL and more preferably 5 to 10 mL relative to 1 g of the compound (2). When the amount of the organic solvent used is within this range, sufficient levels of reactivity and stirrability can be achieved.

The reaction in step A is performed, for example, by a procedure in which the compound (2), the compound (3), the quaternary onium salt, the base, and the organic solvent are mixed and stirred for a predetermined period of time. The reaction temperature in this case is preferably 50 to 100° C. and more preferably 60 to 90° C. When the reaction is performed at a temperature within this range, it is possible to maintain a high reaction speed and, at the same time, reduce the formation of the compound (E-1). This reaction may be performed under pressure.

The compound (4) formed in step A can be isolated or purified, for example, by a combination of common methods such as neutralization, extraction, filtration, concentration, crystallization, recrystallization, distillation, and column chromatography. The compound (4) as formed may be used in production of the compound (1) (hydrolysis of the cyano group) without isolation or purification.

[Step B]

This step comprises: a step of reacting the compound (4) and the compound (5) to form a salt (4') (step B1); and a step of removing the protecting group $P^1$ of the salt (4') to form a compound (6) (step B2).

[Step B1]

This step is a step of mixing the compound (4) and the compound (5) to form the salt (4').

[Chemical Formula 18]

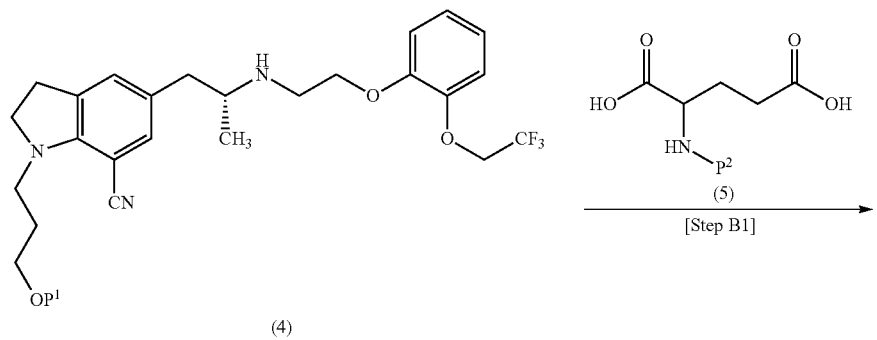

(4)

-continued

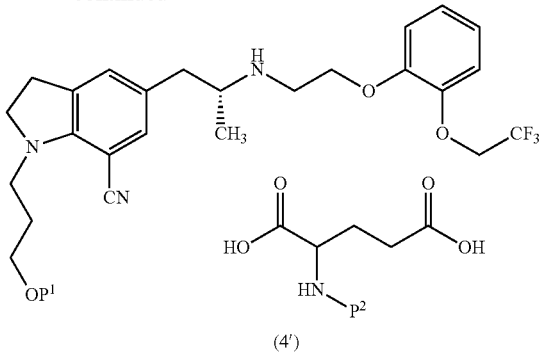

(4')

wherein $P^1$ is a protecting group for a hydroxy group and $P^2$ is a protecting group for an amino group.

Compound (4)

The compound (4) used in step B1 can be produced, for example, by reference to Patent Literature 1.

[Chemical Formula 19]

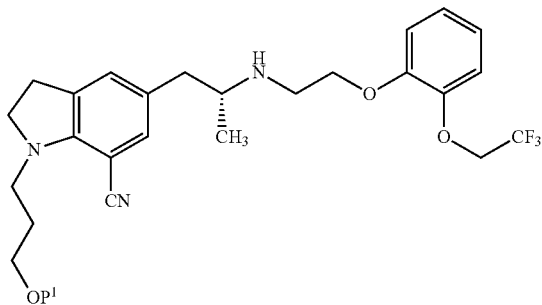

(4)

wherein $P^1$ is a protecting group for a hydroxy group.

For the formula (4), the protecting group $P^1$ is not particularly limited as long as it is a protecting group for a hydroxy group. Examples of the protecting group $P^1$ include: alkyl groups such as a methyl group and a t-butyl group; aralkyl groups such as a benzyl group (Bn) and a p-methoxybenzyl group (PMB); acyl groups such as an acetyl group (Ac), a pivaloyl group (Piv), and a benzoyl group (Bz); a trimethylsilyl group (TMS); a t-butyldimethylsilyl group (TBDMS); a triisopropylsilyl group (TIPS); and a t-butyldiphenylsilyl group (TBDPS), and the protecting group $P^1$ is preferably an aralkyl group or an acyl group and more preferably a benzyl group or a benzoyl group.

Compound (5)

[Chemical Formula 20]

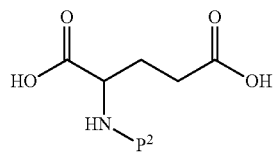

(5)

wherein $P^2$ is a protecting group for an amino group.

The compound (5) used in step B1 refers to a glutamic acid in which a hydrogen atom on nitrogen is substituted (protected) by the protecting group $P^2$. It is preferable for the glutamic acid to be L-glutamic acid. The protecting group $P^2$ is not limited as long as a protecting group for an amino group. Examples of the protecting group $P^2$ include: alkyl groups such as a methyl group and a t-butyl group; alkyl groups such as a benzyl group (Bn) and a p-methoxybenzyl group (PMB); acyl groups such as an acetyl group (Ac), a pivaloyl group (Piv), and a benzoyl group (Bz); and oxycarbonyl groups such as a t-butoxycarbonyl group (Boc), a benzyloxycarbonyl group (Cbz), a 9-fluorenylmethyloxycarbonyl group (Fmoc), a 2,2,2-trichloroethoxycarbonyl group (Troc), and an allyloxycarbonyl group (Alloc), and the protecting group $P^2$ is preferably an acyl group and more preferably an acetyl group.

The amount of the compound (5) used is preferably 0.5 to 1.5 moles and more preferably 0.7 to 1.2 moles relative to 1 mole of the compound (4). When the amount of the compound (5) used is within this range, sufficient salification takes place.

For the reaction in step B1, the compound (4) and the compound (5) may be stirred in the absence of any solvent or may be stirred in a solvent. It is preferable to stir the compound (4) and the compound (5) in a solvent in terms of improving stirrability and homogeneity. In addition, this step may be performed under heating.

The solvent used in step B1 is not particularly limited as long as it does not inhibit the formation of the salt (4'), and examples of the solvent include: water; alcohols such as methanol, ethanol, isopropyl alcohol, and t-butyl alcohol; carboxylic acid esters such as ethyl acetate, isopropyl acetate, and butyl acetate; nitriles such as acetonitrile and propionitrile; sulfoxides such as dimethyl sulfoxide and diethyl sulfoxide; and aromatic hydrocarbons such as toluene and xylene, and the solvent is preferably water, an alcohol, a carboxylic acid ester, a nitrile, or a sulfoxide and more preferably water, isopropyl alcohol, ethyl acetate, acetonitrile, or dimethyl sulfoxide. These solvents may be used alone or two or more thereof may be used as a mixture.

The amount of the solvent used is preferably 5 to 40 mL and more preferably 15 to 25 mL relative to 1 g of the compound (4).

The reaction temperature (heating temperature) in step B1 is preferably 40 to 90° C. and more preferably 50 to 70° C. When the temperature is within this range, the formation of the salt (4') smoothly proceeds without precipitation of the formed salt.

In step B1, a crystal of the salt (4') can be precipitated by leaving the solution containing the formed salt (4'). In this case, the solution (solution containing the salt) may be cooled or concentrated, or a poor solvent (a solvent with a low ability to dissolve the salt (4')) may be added, to precipitate the crystal.

The salt (4') obtained in step B1 has a very low content of the compound (E-1) as an impurity, and thus the salt (4') as obtained can be used in step B2 without any problem. The salt (4') obtained in step B1 may be used in step B2 after being subjected to isolation by filtration or the like and optionally to washing with a solvent and drying.

[Step B2]

This step is a step of subjecting the salt (4') to reaction under conditions which allow removal of the protecting group $P^1$ and thereby forming the compound (6). In step B2, removal of the protecting group $P^1$ and desalination (removal of the compound (5)) may be performed simultaneously or desalination may be performed after removal of the protecting group $P^1$.

[Chemical Formula 21]

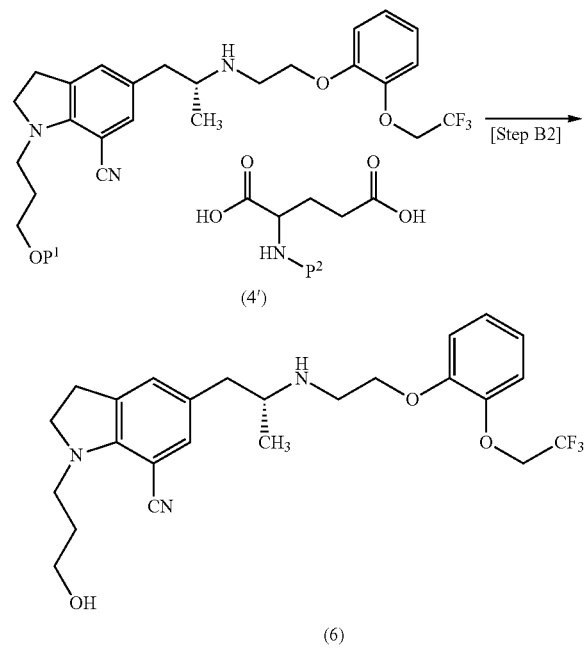

wherein $P^1$ is a protecting group for a hydroxy group and $P^2$ is a protecting group for an amino group.

Step B2 is not particularly limited as long as it is performed under conditions which allow removal of the protecting group $P^1$ of the salt (4'). It is preferable to perform desalination simultaneously in step B2. When desalination is performed simultaneously, it is preferable to perform the removal of the protecting group $P^1$ in a solvent in the presence of a base.

Examples of the base used in step B2 include: alkali metal hydroxides such as sodium hydroxide and potassium hydroxide; alkaline-earth metal hydroxides such as calcium hydroxide; alkali metal carbonates such as sodium carbonate and potassium carbonate; alkaline-earth metal carbonates such as calcium carbonate; alkali metal hydrogen carbonates such as sodium hydrogen carbonate and hydrogen carbonate potassium; alkali metal alkoxides such as sodium methoxide, sodium ethoxide, potassium methoxide, and potassium ethoxide; and alkaline-earth metal alkoxides such as calcium methoxide, and the base is preferably an alkali metal hydroxide and more preferably sodium hydroxide or potassium hydroxide. These bases may be used alone or two or more thereof may be used as a mixture.

The amount of the base used is preferably 1 to 10 moles and more preferably 3 to 5 moles relative to 1 mole of the salt (4').

Examples of the solvent used in step B2 include: water; alcohols such as methanol, ethanol, isopropyl alcohol, and t-butyl alcohol; carboxylic acid esters such as ethyl acetate, isopropyl acetate, and butyl acetate; nitriles such as acetonitrile and propionitrile; sulfoxides such as dimethyl sulfoxide and diethyl sulfoxide; and aromatic hydrocarbons such as toluene and xylene, among which water, alcohols, carboxylic acid esters, nitriles, or sulfoxides is preferably used, and water, isopropyl alcohol, ethyl acetate, acetonitrile or dimethyl sulfoxide is more preferably used. These solvents may be used alone or two or more thereof may be used as a mixture.

The amount of the solvent used is preferably 1 to 10 mL and more preferably 2 to 5 mL relative to 1 g of the salt (4').

The reaction temperature (heating temperature) in step B2 is preferably 20 to 70° C. and more preferably 45 to 55° C. When the temperature is within this range, the removal of the protecting group $P^1$ and the desalination (formation of the compound (6)) proceed smoothly without precipitation of the compound (4).

The compound (6) obtained in step B2 can be isolated or purified by a combination of common methods such as neutralization, extraction, filtration, concentration, crystallization, recrystallization, distillation, and column chromatography. The compound (6) may be used in production of the compound (1) without isolation or purification.

[Step C]

This step is a step of hydrolyzing the cyano group of the compound (6) to form the compound (1).

[Chemical Formula 22]

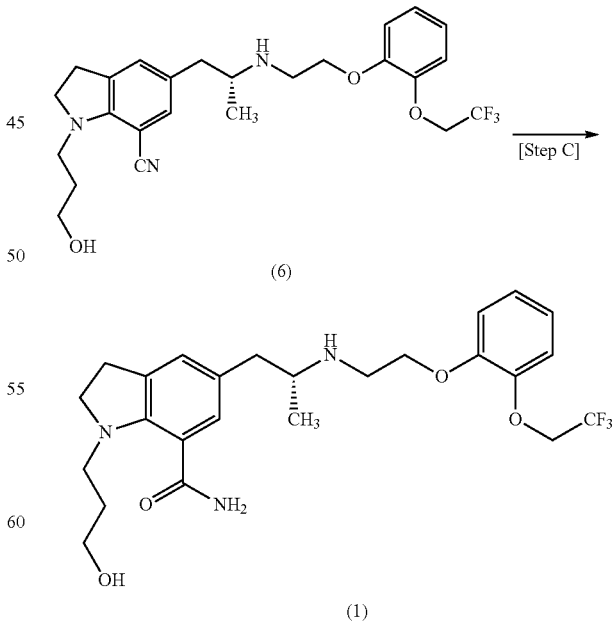

This step can be performed by a method described, for example, in Patent Literature 1.

Next, a method for producing a γ-crystal of the compound (1), which is another embodiment of the present invention, will be described in detail.

The crystal of the compound (1) according to the present embodiment is a γ-crystal of the compound (1) that is substantially free of the compound (E-3) and for which [Y−X] (i.e. a difference between Y and X) is less than 0.040% when the content of the compound (E-3) with respect to the total amount of the crystal is expressed as X % and the content of the compound (E-3) as measured after heating of the crystal at 70° C. for 192 hours is expressed as Y %.

[Chemical Formula 23]

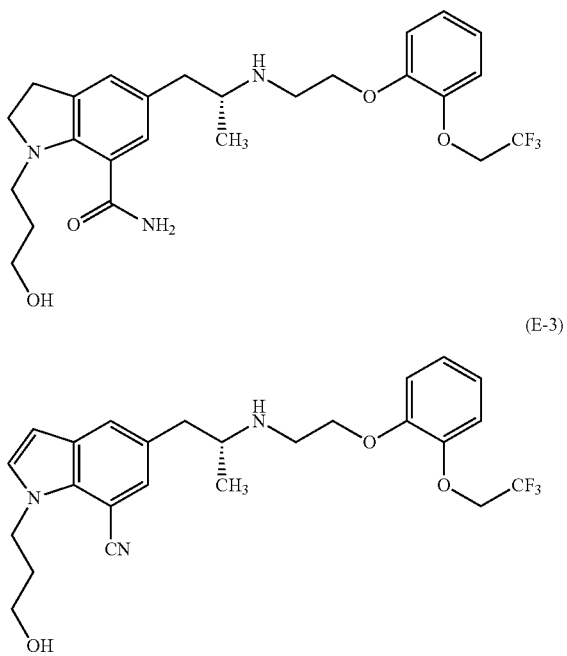

(1)

(E-3)

In the present specification, a "γ-crystal with good stability" is identified by the thermal stability test described later and is one for which [Y−X] (i.e. a difference between Y and X) is less than 0.040% when the content of the compound (E-3) with respect to the total amount of the crystal is expressed as X % and the content of the compound (E-3) as measured after heating of the crystal at 70° C. for 192 hours is expressed as Y %. The crystal structure of the indoline compound is determined using a powder X-ray diffractometer.

The thermal stability test is a test for evaluating a change in the content of the compound (E-3) in the γ-crystal of the compound (1) caused when the crystal is heated at 70° C. for 192 hours. The pre-test content X (%) of the compound (E-3) with respect to the total amount of the crystal and the post-heating content Y (%) of the compound (E-3) with respect to the total amount of the crystal are measured, and the amount of change is calculated by the formula Y−X and expressed as [Y−X]. The content of the compound (E-3) may be on a mass basis or a volume basis. To measure the content of the compound (E-3) with increased accuracy, the measurement may be performed using high-performance liquid chromatography (HPLC). When the content of the compound (E-3) is measured using HPLC, the content can be measured as a value obtained as follows: a peak area of a peak observed in a chromatogram and attributed to the compound (E-3) is divided by the sum of the peak areas of all the peaks.

The γ-crystal of the compound (1) according to the present embodiment may contain the compound (E-3) as an impurity but is preferably substantially free of the compound (E-3). Here, "substantially free" means that the content of the compound (E-3) in the γ-crystal of the compound (1) is within such a range that the pharmacological effect of the compound (1) is not affected. The range is, for example, from 0.001 to 0.200% with respect to the total amount of the crystal.

It is preferable that the γ-crystal of the compound (1) used as an effective ingredient of a medicine be substantially free of the compound (E-3); however, in consideration of production of the medicine, the γ-crystal of the compound (1) may contain the compound (E-3) in an amount of 0.001 to 0.200%. Even a γ-crystal of the compound (1) in which the content of the compound (E-3) is equal to or less than the lower limit is sufficiently usable.

A γ-crystal of the compound (1) for which [Y−X] (i.e. a difference between Y and X) determined in the thermal stability test is less than 0.040% is excellent in terms of thermal stability and is expected to be effective as a crystal for oral solid medicine.

The γ-crystal of the compound (1) according to the present embodiment may contain a solvent (e.g., a solvent used for crystallization) as an impurity, but is preferably substantially free of any solvent. Here, "substantially free" means that the content of the solvent in the γ-crystal of the compound (1) is within such a range that the pharmacological effect of the compound (1) is not affected. When the γ-crystal contains a solvent, the residual solvent amount in the γ-crystal of the compound (1) is preferably 5000 ppm or less, more preferably 890 ppm or less, and particularly preferably 500 ppm or less. The lower limit of the content of the solvent is, for example, a lower detection limit in gas chromatography and is, for example, 10 ppm. The residual solvent amount as defined herein refers to the amount of the residue of the solvent used for crystallization in the resulting crystal. The upper limit of the residual solvent amount is appropriately set on the basis of the standard for residual solvents which is specified in guidelines provided by International Conference on Harmonisation of Technical Requirements for Registration of Pharmaceuticals for Human Use (ICH).

As described later, the γ-crystal of the compound (1) is superior in stability to light and crushing to the α-crystal which has been conventionally considered favorable, and is more effective as a crystal for oral solid medicine than the α-crystal. Furthermore, in view of the reduced amount of the residual solvent, the γ-crystal of the compound (1) is expected to be effective, for example, as an active ingredient of an oral medicine for treatment of dysuria.

(Method for Producing γ-Crystal with Good Stability)

The solvent used in the method for producing the γ-crystal is an alcohol solvent represented by the formula (7)

[Chemical Formula 24]

ROH (7)

wherein R is an alkyl group having 1 to 4 carbon atoms, or a mixed solvent of the alcohol solvent and an ether solvent represented by the formula (8)

[Chemical Formula 25]

(8)

wherein R is an alkyl group having 1 to 4 carbon atoms and R¹ is a branched or cyclic alkyl group having 3 to 6 carbon atoms.

Examples of the alkyl group having 1 to 4 carbon atoms include a methyl group, an ethyl group, a propyl group, and a butyl group. Examples of the branched alkyl group having 3 to 6 carbon atoms include an isopropyl group, an isobutyl group, a sec-butyl group, and a t-butyl group, and examples of the cyclic alkyl group having 3 to 6 carbon atoms include a cyclopropyl group, a cyclobutyl group, and a cyclopentyl group.

In terms of ease of crystallization and reduction in residual solvent amount, at least one solvent selected from the group consisting of methanol, ethanol, 2-propyl alcohol (isopropyl alcohol), 2-butyl alcohol (sec-butyl alcohol), and 2-methyl-2-propyl alcohol (t-butyl alcohol) is used as the alcohol solvent.

In terms of ease of crystallization and reduction in residual solvent amount, it is preferable for the ether solvent to be at least one solvent selected from the group consisting of diisopropyl ether, t-butyl methyl ether, and cyclopentyl methyl ether.

The compound (1) used in step C is not particularly limited, as long as it is in a solvent-soluble form so that it can be thoroughly dissolved in the solvent defined above in crystallization. That is, the compound (1) is specifically in a crystalline state or a solid state and, when in a crystalline state, it is not required to take a particular crystal form. The compound (1) may be a hydrate or a solvate.

Specifically, the crystallization is performed, for example, by a method in which the compound (1) is dissolved in a solvent and then the γ-crystal is precipitated by cooling.

The dissolution of the compound (1) in a solvent is accomplished by mixing the compound (1) and the solvent, and heating may be performed to thoroughly dissolve the compound (1). The heating temperature in that case is not particularly limited as long as it is a temperature which allows thorough dissolution of the compound (1) in the solvent, and the heating temperature is preferably 40 to 90° C.

The amount of the solvent used to dissolve the compound (1) is preferably 10 to 40 mL and more preferably 10 to 20 mL relative to 1 g of the compound (1). When the amount of the solvent used is within this range, the compound (1) can be thoroughly dissolved in the solvent, and the γ-crystal is precipitated quickly by cooling.

After the compound (1) is dissolved in the solvent, the resulting solution may be cooled to precipitate the γ-crystal. The cooling temperature in that case is not particularly limited as long as it is a temperature which allows precipitation of the γ-crystal of the compound (1), and the cooling temperature is preferably 15 to 25° C.

In precipitation of the γ-crystal, it is desirable to add a separately synthesized γ-crystal of the compound (1) as a seed crystal in order to promote the precipitation (formation and growth) of the γ-crystal. The γ-crystal of the compound (1) added as a seed crystal may be, for example, one produced by the method described in Patent Literature 3. The amount of the seed crystal used is not particularly limited as long as it is an amount which allows promotion of the precipitation of the γ-crystal, and the amount of the seed crystal used is preferably 1 to 50 mg and more preferably 1 to 10 mg relative to 1 g of the compound (1) used.

The precipitated γ-crystal can be collected by filtration followed by drying under reduced pressure. The γ-crystal of the compound (1) can be used, for example, as an active ingredient of an oral medicine for treatment of dysuria.

EXAMPLES

Next, the present invention will be specifically described with reference to Examples; however, the scope of the present invention is not limited by the Examples.

Examples of Step A

Compound analysis was performed by the following equipment and method.

Analytical equipment: High-performance liquid chromatography (manufactured by Shimadzu Corporation)

Analytical Conditions:

Detector: Ultraviolet absorptiometer (measurement wavelength: 254 nm)

Column: Inertsil ODS-3 (GL Sciences Inc., 5 μm, 4.6 mm×15 cm)

Column temperature: 40° C.

Mobile phase and measurement method: 1.0 g of ammonium formate and water were mixed to a volume of 1000 mL, and then 0.53 mL of formic acid was added to adjust the pH of the solution to 3.7. The measurement was performed as the volume ratio between the solution and acetonitrile was varied from 3:7 to 9:1.

Flow rate: 1.0 mL/minute

Example A1 (Synthesis of 3-{7-cyano-5-[(2R)-2-({2-[2-(2,2,2-trifluoroethoxy)phenoxy]ethyl}amino)propyl]-2,3-dihydro-1H-indol-1-yl}propyl benzoate)

In a container having an inner volume of 5 L and equipped with a reflux condenser, a thermometer, and a stirrer, 317 g (0.62 moles) of 3-{5-[(2R)-2-aminopropyl]-7-cyano-2,3-dihydro-1H-indol-1-yl}propio benzoate.mono-(2R,3R)-tartrate, 1.8 L of ethyl acetate, and 1280 g (1.83 moles) of a 20% aqueous potassium carbonate solution were mixed and stirred at room temperature for 1 hour.

After completion of the stirring, an organic phase was separated from the reaction liquid, and the obtained organic phase was concentrated under reduced pressure. The concentrate, 1.8 L of acetonitrile, 69 g (0.65 moles) of sodium carbonate, 10 g (0.03 moles) of tetrabutylammonium bromide, and 233 g (0.74 moles) of 2-[2-(2,2,2-trifluoroethoxy)phenoxy]ethyl methanesulfonate were mixed and subjected to reaction under stirring at 75 to 85° C. for 30 hours.

After completion of the reaction, the reaction liquid was cooled to room temperature and then filtered, with the result that 2.2 kg of an acetonitrile solution of 3-({7-cyano-5-[(2R)-2-({2-[2-(2,2,2-trifluoroethoxy)phenoxy]ethyl}amino)propyl]-2,3-dihydro-1H-indol-1-yl}propyl benzoate (content: 14.2 mass %, 0.53 moles) was obtained (yield: 85%).

Comparative Example A1 (Synthesis of 3-{7-cyano-5-[(2R)-2-({2-[2-(2,2,2-trifluoroethoxy)phenoxy]ethyl}amino)propyl]-2,3-dihydro-1H-indol-1-yl}propyl benzoate)

In Example A1, a reaction was performed in the similar manner as in Example A1, except that tetrabutylammonium bromide was not added.

As a result, the yield of 3-{7-cyano-5-[(2R)-2-({2-[2-(2,2,2-trifluoroethoxy)phenoxy]ethyl}amino)propyl]-2,3-dihydro-1H-indol-1-yl}propyl benzoate was 77%.

Example A2 (Synthesis of 3-{7-cyano-5-[(2R)-2-({2-[2-(2,2,2-trifluoroethoxy)phenoxy]ethyl}amino)propyl]-2,3-dihydro-1H-indol-1-yl}propyl benzoate)

In Example A2, a reaction was performed in the similar manner as in Example A1, except that the organic solvent was replaced by toluene.

As a result, the yield of 3-{7-cyano-5-[(2R)-2-({2-[2-(2,2,2-trifluoroethoxy)phenoxy]ethyl}amino)propyl]-2,3-dihydro-1H-indol-1-yl}propyl benzoate was 82%.

Comparative Example A2 (Synthesis of 3-{7-cyano-5-[(2R)-2-({2-[2-(2,2,2-trifluoroethoxy)phenoxy]ethyl}amino)propyl]-2,3-dihydro-1H-indol-1-yl}propyl benzoate)

In Comparative Example A2, a reaction was performed in the similar manner as in Comparative Example A1, except that the organic solvent was replaced by toluene.

As a result, the yield of 3-{7-cyano-5-[(2R)-2-({2-[2-(2,2,2-trifluoroethoxy)phenoxy]ethyl}amino)propyl]-2,3-dihydro-1H-indol-1-yl}propyl benzoate was 71%.

The above results reveal that the reaction speed between the compound (2) and the compound (3) is increased by the presence of a quaternary ammonium.

Examples of Step B

Reference Example B (Synthesis of 3-{7-cyano-5-[(2R)-2-({2-[2-(2,2,2-trifluoroethoxy)phenoxy]ethyl}amino)propyl]-2,3-dihydro-1H-indol-1-yl}propyl benzoate)

In a container having an inner volume of 5 L and equipped with a reflux condenser, a thermometer, and a stirrer, 317 g (0.62 moles) of 3-{5-[(2R)-2-aminopropyl]-7-cyano-2,3-dihydro-1H-indol-1-yl}propyl benzoate.mono-(2R,3R)-tartrate, 1.8 L of ethyl acetate, and 1280 g (1.83 moles) of a 20% aqueous potassium carbonate solution were mixed and stirred at room temperature for 1 hour.

After completion of the stirring, an organic phase was separated from the reaction liquid, and the obtained organic phase was concentrated under reduced pressure. The concentrate, 1.8 L of acetonitrile, 69 g (0.65 moles) of sodium carbonate, 10 g (0.03 moles) of tetrabutylammonium bromide, and 233 g (0.74 moles) of 2-[2-(2,2,2-trifluoroethoxy)phenoxy]ethyl methanesulfonate were mixed and subjected to a reaction under stirring at 75 to 85° C. for 30 hours.

After completion of the reaction, the reaction liquid was cooled to room temperature and then filtered, with the result that 2.2 kg of an acetonitrile solution of 3-{7-cyano-5-[(2R)-2-({2-[2-(2,2,2-trifluoroethoxy)phenoxy]ethyl}amino)propyl]-2,3-dihydro-1H-indol-1-yl}propyl benzoate (content: 14.2 mass %, 0.53 moles) was obtained (yield: 85%).

Example B1 (Synthesis of 3-{7-cyano-5-[(2R)-2-({2-[2-(2,2,2-trifluoroethoxy)phenoxy]ethyl}amino)propyl]-2,3-dihydro-1H-indol-1-yl}propyl benzoate.mono-N-acetylglutamate)

In 3-{7-cyano-5-[(2R)-2-({2-[2-(2,2,2-trifluoroethoxy)phenoxy]ethyl}amino)propyl]-2,3-dihydro-1H-indol-1-yl}propyl benzoate (compound corresponding to the compound (4) wherein $P^1$ is a benzoyl group) used in this example, the content of the compound (E-1) was 12.3%.

In a container having an inner volume of 10 L and equipped with a reflux condenser, a thermometer, and a stirrer, the acetonitrile solution of 3-{7-cyano-5-[(2R)-2-({2-[2-(2,2,2-trifluoroethoxy)phenoxy]ethyl}amino)propyl]-2,3-dihydro-1H-indol-1-yl}propyl benzoate obtained in Reference Example 1 and 3.9 L of acetonitrile were mixed, and the mixed liquid was heated to 50 to 60° C.

Subsequently, 143 mL of a dimethyl sulfoxide solution of 116.7 g (0.62 moles) N-acetylglutamic acid was added to the mixed liquid, to which 0.12 g of (3-{7-cyano-5-[(2R)-2-({2-[2-(2,2,2-trifluoroethoxy)phenoxy]ethyl}amino)propyl]-2,3-dihydro-1H-indol-1-yl}propyl benzoate.mono-N-acetylglutamate was then added as a seed crystal. This was followed by stirring at 50 to 60° C. for 2 hours.

After completion of the stirring, the mixed liquid was cooled to 0° C., and the crystal precipitated was filtered. The resulting crystal was washed with 1.6 L of cooled acetonitrile and then dried to obtain 398 g (0.52 moles) of 3-{7-cyano-5-[(2R)-2-({2-[2-(2,2,2-trifluoroethoxy)phenoxy]ethyl}amino)propyl]-2,3-dihydro-1H-indol-1-yl}propyl benzoate.mono-N-acetylglutamate in the form of a colorless, transparent crystal (yield: 98%).

In this case, the content of the dialkylated compound was reduced below the detection limit.

It should be noted that 3-{7-cyano-5-[(2R)-2-({2-[2-(2,2,2-trifluoroethoxy)phenoxy]ethyl}amino)propyl]-2,3-dihydro-1H-indol-1-yl}propyl benzoate.mono-N-acetylglutamate is a novel compound characterized by the following physical property values.

Melting point: 142 to 148° C.

$^1$H-NMR (DMSO-$d_6$, δ (ppm)): 0.95 (3H, d), 1.74 to 1.81 (1H, m), 1.84 (3H, s), 1.86 to 1.91 (1H, m), 2.03 to 2.10 (2H, m), 2.23 to 2.28 (2H, m), 2.35 (1H, dd), 2.66 (1H, dd), 2.88 to 3.04 (5H, m), 3.57 (2H, t), 3.68 (2H, t), 4.07 (2H, t), 4.14 to 4.19 (1H, m), 4.38 (2H, t), 4.66 (2H, q), 6.90 to 7.10 (6H, m), 7.50 (2H, t), 7.65 (1H, t), 7.96 (1H, s), 7.99 (2H, d)

Example B2 (Synthesis of 1-(3-hydroxypropyl)-5-[(2R)-2-({2-[2-(2,2,2-trifluoroethoxy)phenoxy]ethyl}amino)propyl]-2,3-dihydro-1H-indole-7-carbonitrile)

In a container having an inner volume of 10 L and equipped with a reflux condenser, a thermometer, and a stirrer, 285 g (0.37 moles) of 3-{7-cyano-5-[(2R)-2-({2-[2-(2,2,2-trifluoroethoxy)phenoxy]ethyl}amino)propyl]-2,3-dihydro-1H-indol-1-yl}propyl benzoate.mono-N-acetylglutamate obtained in Example B1, 370 g (1.52 moles) of a 23 mass % aqueous potassium hydroxide solution, and 720 mL of methanol were mixed and subjected to a reaction under stirring at 45 to 50° C. for 1 hour.

After completion of the reaction, the reaction liquid was cooled to room temperature, which was followed by addition of 850 mL of water and 2540 mL of ethyl acetate, then thorough stirring, and then separation of an organic layer. The obtained organic layer was washed with an aqueous sodium hydrogen carbonate solution and an aqueous ammonium chloride solution, was then concentrated under reduced pressure and, after addition of 360 mL of ethanol, was concentrated under reduced pressure to obtain 175 g (0.37 moles) of 1-(3-hydroxypropyl)-5-[(2R)-2-({2-[2-(2,2,2-trifluoroethoxy)phenoxy]ethyl}amino)propyl]-2,3-dihydro-1H-indole-7-carbonitrile (yield: 99%).

Examples B2 to B4 and Comparative Examples B1 to B32 (Synthesis of 3-{7-cyano-5-[(2R)-2-({2-[2-(2,2,2-trifluoroethoxy)phenoxy]ethyl}amino)propyl]-2,3-dihydro-1H-indol-1-yl}propyl benzoate-mono-N-acetylglutamate)

Reactions were performed in the similar manner as in Example B1, except that the type of the acid was varied from that in Example B1. The results are shown in Table 1.

TABLE 1

| | Acid | Solvent | State | Content of compound (E-1) [%] |
|---|---|---|---|---|
| Example B1 | N-acetylglutamic acid | Acetonitrile/Dimethyl sulfoxide | Crystal | <0.1 |
| Example B2 | N-acetylglutamic acid | Acetonitrile | Crystal | 0.1 |
| Example B3 | N-acetylglutamic acid | Isopropyl alcohol | Crystal | 1.2 |
| Comparative Example B1 | Oxalic acid | Isopropyl alcohol | Crystal | 3 |
| Comparative Example B2 | L-tartaric acid | Isopropyl alcohol | Oily | — |
| Comparative Example B3 | D-tartaric acid | Isopropyl alcohol | Crystal | 9.2 |
| Comparative Example B4 | N-acetylphenylalanine | Toluene | Crystal | 1.6 |
| Comparative Example B5 | N-acetylphenylalanine | Ethyl acetate | Crystal | 3.8 |
| Comparative Example B6 | N-acetylphenylalanine | Isopropyl alcohol | Solution | — |
| Comparative Example B7 | Sulfuric acid | Isopropyl alcohol | Crystal | 4.7 |
| Comparative Example B8 | Phthalic acid | Isopropyl alcohol | Oily | — |
| Comparative Example B9 | Maleic acid | Isopropyl alcohol | Solution | — |
| Comparative Example B10 | Fumaric acid | Isopropyl alcohol | Oily | — |
| Comparative Example B11 | Malonic acid | Isopropyl alcohol | Solution | — |
| Comparative Example B12 | Succinic acid | Isopropyl alcohol | Solution | — |
| Comparative Example B13 | L-malic acid | Isopropyl alcohol | Oily | — |
| Comparative Example B14 | Hydrochloric acid | Isopropyl alcohol | Solution | — |
| Comparative Example B15 | Hydrobromic acid | Isopropyl alcohol | Solution | — |
| Comparative Example B16 | Phosphoric acid | Isopropyl alcohol | Oily | — |
| Comparative Example B17 | P-toluenesulfonic acid | Isopropyl alcohol | Solution | — |
| Comparative Example B18 | Methanesulfonic acid | Isopropyl alcohol | Solution | — |
| Comparative Example B19 | Benzenesulfonic acid | Isopropyl alcohol | Solution | — |
| Comparative Example B20 | (−)-camphorsulfonic acid | Isopropyl alcohol | Solution | — |
| Comparative Example B21 | (+)-camphorsulfonic acid | Isopropyl alcohol | Solution | — |
| Comparative Example B22 | Benzoic acid | Isopropyl alcohol | Solution | — |
| Comparative Example B23 | P-nitrobenzoic acid | Isopropyl alcohol | Oily | — |
| Comparative Example B24 | P-chlorobenzoic acid | Isopropyl alcohol | Solution | — |
| Comparative Example B25 | P-hydroxybenzoic acid | Isopropyl alcohol | Solution | — |
| Comparative Example B26 | N-acetylcysteine | Isopropyl alcohol | Solution | — |
| Comparative Example B27 | N-acetylglycine | Isopropyl alcohol | Solution | — |
| Comparative Example B28 | N-acetylaspartic acid | Isopropyl alcohol | Solution | — |
| Comparative Example B29 | Ascorbic acid | Isopropyl alcohol | Oily | — |
| Comparative Example B30 | Citric acid | Isopropyl alcohol | Oily | — |

TABLE 1-continued

|  | Acid | Solvent | State | Content of compound (E-1) [%] |
|---|---|---|---|---|
| Comparative Example B31 | Acetic acid | Isopropyl alcohol | Solution | — |
| Comparative Example 32 | Trifluoroacetic acid | Isopropyl alcohol | Solution | — |

The above results show that, in most cases of the used acids, a salt with 3-{7-cyano-5-[(2R)-2-({2-[2-(2,2,2-trifluoroethoxy)phenoxy]ethyl}amino)propyl]-2,3-dihydro-1H-indol-1-yl}propyl benzoate could not be obtained in the form of a solid crystal, while a salt of the compound and N-acetylglutamic acid could be obtained in the form of a crystal from all solvents.

It was also found that among the salts obtained in the form of a crystal, those obtained when using N-acetylglutamic acid as an acid had a very low content of the compound (E-1).

Examples of Step C (Compound Analysis)

Compound analysis was performed in the same manner as in the above examples of step A, except that the measurement wavelength and the mobile phase were changed as follows.

Measurement wavelength: 225 nm

Mobile phase and measurement method: 1.0 g of ammonium formate and water were mixed to a volume of 1000 mL, and then 0.53 mL of formic acid was added to adjust the pH of the solution to 3.7. The measurement was performed as the volume ratio between the solution and acetonitrile was varied from 4:1 to 1:1.

The content of the compound (E-3) was expressed as a value calculated as follows: a peak area of a peak observed in a chromatogram and attributed to the compound (E-3) was divided by the sum of peak areas of all peaks observed in the chromatogram.

(Crystal Structure Analysis)

Analysis equipment: Powder X-ray diffractometer, RINT-TTR III (manufactured by Rigaku Corporation)

Example C1 (Production of γ-Crystal of Compound (1) Using Isopropyl Alcohol Solvent)

In a container having an inner volume of 300 mL and equipped with a reflux condenser, a thermometer, and a thermometer there were put 30 g of the compound (1) and 300 mL of isopropyl alcohol, which were heated to 45° C. to thoroughly dissolve the compound (1).

The dissolution was followed by cooling to decrease the solution temperature to 35° C., then by addition of 3 mg of a γ-crystal of the compound (1) as a seed crystal, then by natural cooling at room temperature overnight, and then by cooling to decrease the solution temperature to 6° C. The resulting crystal precipitated was filtered.

Subsequently, the obtained crystal (filtered product) was dried by heating (45° C.) under reduced pressure to obtain 23 g of a γ-crystal of the compound (1) in the form of a white crystal (yield: 79%).

The amount of the residual solvent in the obtained crystal was 495 ppm.

(Thermal Stability Test)

A thermal stability test was conducted on the γ-crystal obtained in Example C1.

Content (X) of compound (E-3) measured before test: 0.043%

Content (Y) of compound (E-3) measured after test: 0.044%

[Y−X] was 0.001%, i.e., the increase in the content of the compound (E-3) observed during the test was small, which means that the γ-crystal was stable.

Comparative Example C1 (Production of γ-Crystal of Compound (1) Using Toluene Solvent)

In a container having an inner volume of 300 mL and equipped with a reflux condenser, a thermometer, and a thermometer there were put 15 g of the compound (1) and 300 mL of toluene, which were heated to 65° C. to thoroughly dissolve the compound (1).

The dissolution was followed by repeated cycles of heating and cooling to decrease the solution temperature to 23° C., and the resulting crystal precipitated was filtered. The filterability was good.

Subsequently, the obtained crystal (filtered product) was dried by heating (45° C.) under reduced pressure to obtain 15 g of a γ-crystal of the compound (1) in the form of a white crystal (yield: 98%).

The amount of the residual solvent in the obtained crystal was 2564 ppm.

(Thermal Stability Test)

A thermal stability test was conducted on the γ-crystal obtained in Comparative Example C1.

Content (X) of compound (E-3) measured before test: 0.091%

Content (Y) of compound (E-3) measured after test: 0.133%

[Y−X] was 0.042%, i.e., the increase in the content of the compound (E-3) observed during the test was large, which means that the γ-crystal was unstable.

Example C2 (Production of γ-Crystal of Compound (1) Using Isopropyl Alcohol Solvent)

In a container having an inner volume of 300 mL and equipped with a reflux condenser, a thermometer, and a thermometer there were put 30 g of the compound (1) and 300 mL of isopropyl alcohol, which were heated to 45° C. to thoroughly dissolve the compound (1).

The dissolution was followed by cooling to decrease the solution temperature to 35° C., then by addition of 50 mg of a γ-crystal of the compound (1) as a seed crystal, and then by repeated cycles of heating and cooling to decrease the solution temperature to 4° C. The resulting crystal precipitated was filtered.

Subsequently, the obtained crystal (filtered product) was dried by heating (45° C.) under reduced pressure to obtain 24 g of a γ-crystal of the compound (1) in the form of a white crystal (yield: 80%).

The amount of the residual solvent in the obtained crystal was 873 ppm.
(Thermal Stability Test)
A thermal stability test was conducted on the γ-crystal obtained in Example C2.
Content (X) of compound (E-3) measured before test: 0.076%
Content (Y) of compound (E-3) measured after test: 0.088%
[Y−X] was 0.012%, i.e., the increase in the content of the compound (E-3) observed during the test was small, which means that the γ-crystal was stable.

Example C3 (Production of γ-Crystal of Compound (1) Using Isopropyl Alcohol and t-Butyl Methyl Ether Solvents)

In a container having an inner volume of 300 mL and equipped with a reflux condenser, a thermometer, and a thermometer there were put 30 g of the compound (1), 100 mL of isopropyl alcohol, and 200 mL of t-butyl methyl ether, which were heated to 45° C. to thoroughly dissolve the compound (1).
The dissolution was followed by cooling to decrease the solution temperature to 5° C., then by addition of 20 mg of a γ-crystal of the compound (1) as a seed crystal, and then by repeated cycles of heating and cooling to decrease the solution temperature to 5° C. The resulting crystal precipitated was filtered. 14-0741
Subsequently, the obtained crystal (filtered product) was dried by heating (45° C.) under reduced pressure to obtain 25 g of a γ-crystal of the compound (1) in the form of a white crystal (yield: 82%).
In the obtained crystal, the amounts of the residual solvents, isopropyl alcohol and t-butyl methyl ether, were 157 ppm and 104 ppm, respectively, and the total amount of the residual solvents was 261 ppm.
(Thermal Stability Test)
A thermal stability test was conducted on the γ-crystal obtained in Example C3.
Content (X) of compound (E-3) measured before test: 0.071%
Content (Y) of compound (E-3) measured after test: 0.097%
[Y−X] was 0.026%, i.e., the increase in the content of the compound (E-3) observed during the test was small, which means that the γ-crystal was stable.

Example C4 (Production of γ-Crystal of Compound (1) Using Isopropyl Alcohol and t-Butyl Methyl Ether Solvents)

In a container having an inner volume of 300 mL and equipped with a reflux condenser, a thermometer, and a thermometer there were put 25 g of the compound (1), 75 mL of isopropyl alcohol, and 225 mL of t-butyl methyl ether, which were heated to 55° C. to thoroughly dissolve the compound (1).
The dissolution was followed by cooling to decrease the solution temperature to 50° C., then by addition of 20 mg of a γ-crystal of the compound (1) as a seed crystal, and then by repeated cycles of heating and cooling to decrease the solution temperature to 5° C. The resulting crystal precipitated was filtered.
Subsequently, the obtained crystal (filtered product) was dried by heating (45° C.) under reduced pressure to obtain 21 g of a γ-crystal of the compound (1) in the form of a white crystal (yield: 85%).

In the obtained crystal, the amounts of the residual solvents, isopropyl alcohol and t-butyl methyl ether, were 16 ppm and 104 ppm, respectively, and the total amount of the residual solvents was 120 ppm.
(Thermal Stability Test)
A thermal stability test was conducted on the γ-crystal obtained in Example C4.
Content (X) of compound (E-3) measured before test: 0.067%
Content (Y) of compound (E-3) measured after test: 0.091%
[Y−X] was 0.024%, i.e., the increase in the content of the compound (E-3) observed during the test was small, which means that the γ-crystal was stable.

Reference Example C1 (Production of Crystal of Compound (1) Using Methyl Isobutyl Ketone Solvent)

In a container having an inner volume of 300 mL and equipped with a reflux condenser, a thermometer, and a thermometer there were put 30 g of the compound (1) and 300 mL of methyl isobutyl ketone, which were heated to 60° C. to thoroughly dissolve the compound (1).
The dissolution was followed by cooling to decrease the solution temperature to 50° C., then by addition of 6 mg of a γ-crystal of the compound (1) as a seed crystal, and then by repeated cycles of heating and cooling to decrease the solution temperature to 20° C. The resulting crystal precipitated was filtered. The filterability was good.
Subsequently, the obtained crystal (filtered product) was dried by heating (45° C.) under reduced pressure to obtain 26 g of a mixed crystal of an α-crystal and a γ-crystal of the compound (1) in the form of a white crystal (yield: 86%).

Reference Example C2 (Production of Crystal of Compound (1) Using Isopropyl Acetate Solvent)

In a container having an inner volume of 300 mL and equipped with a reflux condenser, a thermometer, and a thermometer there were put 15 g of the compound (1) and 300 mL of isopropyl acetate, which were heated to 60° C. to thoroughly dissolve the compound (1).
The dissolution was followed by cooling to decrease the solution temperature to 50° C., then by addition of 16 mg of a γ-crystal of the compound (1) as a seed crystal, and then by repeated cycles of heating and cooling to decrease the solution temperature to 6° C. The resulting crystal precipitated was filtered.
Subsequently, the obtained crystal (filtered product) was dried by heating (45° C.) under reduced pressure to obtain 14 g of a mixed crystal of an α-crystal and a γ-crystal of the compound (1) in the form of a white crystal (yield: 91%).
The above results confirmed that a γ-crystal obtained by the production method of the present invention has good stability to heat and has a low content of the residual solvent.

Reference Example C3 (Photostability Test and Crushing Stability Test)

An α-crystal, a β-crystal, and a γ-crystal were produced, and each of them was subjected to a photostability test and a crushing stability test under the following conditions.
(Conditions of Photostability Test)
Each crystal was left under irradiation of 4000-lux light at 25° C. and a relative humidity of 60% for 336 hours.

(Conditions of Crushing Stability Test)

Each crystal was put in a mortal and crushed with a pestle.

(Production of α-Crystal)

In a container having an inner volume of 300 mL and equipped with a reflux condenser, a thermometer, and a thermometer there were put 10 g of the compound (1) and 130 mL of ethyl acetate, which were heated to 70° C. to thoroughly dissolve the compound (1).

The dissolution was followed by cooling to decrease the solution temperature to 26° C., and the resulting crystal precipitated was filtered.

Subsequently, the obtained crystal (filtered product) was dried by heating (45° C.) under reduced pressure to obtain 9 g of an α-crystal of the compound (1) in the form of a white crystal (yield: 88%).

(Photostability Test)

The photostability test was conducted on the obtained α-crystal.

Content of compound (E-3) measured before photostability test: 0.037%

Content of compound (E-3) measured after photostability test: 0.960%

For the α-crystal, the content of the compound (E-3) was increased by 0.923% as a result of the photostability test.

(Crushing Stability Test)

The crushing stability test was conducted on the obtained α-crystal.

As a result, it was confirmed that the α-crystal is transformed into a γ-crystal.

(Production of β-Crystal)

In a container having an inner volume of 2000 mL and equipped with a reflux condenser, a thermometer, and a thermometer there were put 60 g of the compound (1) and 900 mL of isopropyl acetate, which were heated to 60° C. to thoroughly dissolve the compound (1).

The dissolution was followed by cooling to decrease the solution temperature to 20° C., and the resulting crystal precipitated was filtered.

Subsequently, the obtained crystal (filtered product) was dried by heating (45° C.) under reduced pressure to obtain 54 g of a β-crystal of the compound (1) in the form of a white crystal (yield: 91%).

(Photostability Test)

The photostability test was conducted on the obtained β-crystal.

Content of compound (E-3) measured before photostability test: 0.027%

Content of compound (E-3) measured after photostability test: 0.419%

For the β-crystal, the content of the compound (E-3) was increased by 0.392% as a result of the photostability test.

(Crushing Stability Test)

The crushing stability test was conducted on the obtained β-crystal.

As a result, phase transition was not observed after the crushing.

(Production of γ-Crystal)

In a container having an inner volume of 300 mL and equipped with a reflux condenser, a thermometer, and a thermometer there were put 30 g of the compound (1) and 150 mL of isopropyl alcohol, which were heated to 40° C. to thoroughly dissolve the compound (1).

The dissolution was followed by cooling to decrease the solution temperature to 3° C., and the resulting crystal precipitated was filtered.

Subsequently, the obtained crystal (filtered product) was dried by heating (45° C.) under reduced pressure to obtain 26 g of a γ-crystal of the compound (1) in the form of a white crystal (yield: 86%).

(Photostability Test)

The photostability test was conducted on the obtained γ-crystal.

Content of compound (E-3) measured before photostability test: 0.024%

Content of compound (E-3) measured after photostability test: 0.321%

For the γ-crystal, the content of the compound (E-3) was increased by 0.297% as a result of the photostability test.

(Crushing Stability Test)

The crushing stability test was conducted on the obtained γ-crystal.

As a result, phase transition was not observed after the crushing.

The above results of the photostability test confirmed that the γ-crystal of the present embodiment has good stability to light and that the α-crystal is the most unstable.

The results of the crushing stability test confirmed that the γ-crystal of the present embodiment does not undergo phase transition even when subjected to crushing and is thus considered to have good stability and that the α-crystal is the most unstable.

The invention claimed is:

1. A salt comprising:
a compound represented by the following formula (4):

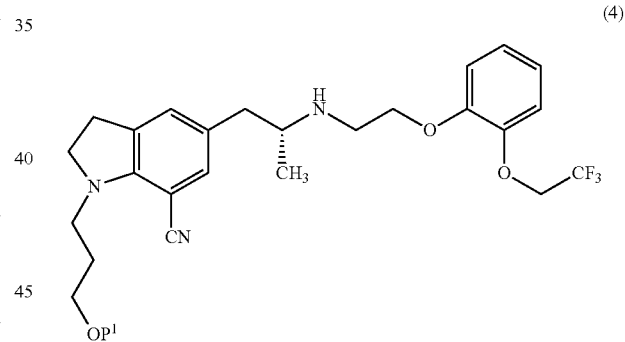

(4)

wherein $P^1$ is a protecting group; and
a compound represented by the following formula (5):

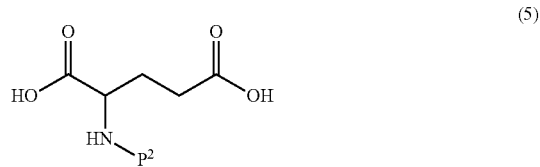

(5)

wherein $P^2$ is a protecting group.

2. The salt according to claim 1, wherein the compound represented by the formula (5) is N-acylglutamic acid.

3. A method for producing the salt according to claim 1, the method comprising:
reacting a compound represented by the following formula (2):

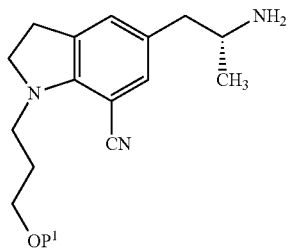

(2)

wherein P¹ is a protecting group,
with a compound represented by the following formula (3):

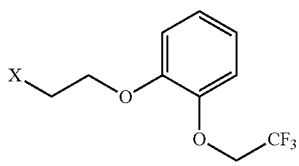

(3)

wherein X is a leaving group,
in the presence of a quaternary onium salt and a base to form the compound represented by the formula (4); and
mixing the compound represented by the formula (4) with the compound represented by the formula (5).

4. The method according to claim 3, wherein the quaternary onium salt is a quaternary ammonium chloride or a quaternary ammonium bromide.

5. A method for producing a compound represented by the following formula (6):

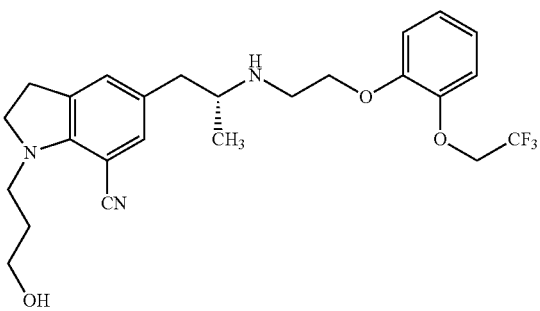

(6)

the method comprising:
removing, from the salt according to claim 1, the protecting group P¹.

* * * * *